US011860070B1

(12) United States Patent
Peterson

(10) Patent No.: US 11,860,070 B1
(45) Date of Patent: Jan. 2, 2024

(54) VOLATILE ORGANIC CHEMICAL IN SOLID SAMPLE COLLECTION, PROCESSING, AND MEASUREMENT APPARATUS AND METHOD

(71) Applicant: James L. Peterson, Princeton, NJ (US)

(72) Inventor: James L. Peterson, Princeton, NJ (US)

( * ) Notice: Subject to any disclaimer, the term of this patent is extended or adjusted under 35 U.S.C. 154(b) by 0 days.

(21) Appl. No.: 18/199,646

(22) Filed: May 19, 2023

(51) Int. Cl.
| G01N 1/04 | (2006.01) |
| G01N 33/24 | (2006.01) |
| G01N 33/00 | (2006.01) |
| G01N 1/28 | (2006.01) |

(52) U.S. Cl.
CPC ............... *G01N 1/04* (2013.01); *G01N 1/286* (2013.01); *G01N 33/0011* (2013.01); *G01N 2001/2866* (2013.01)

(58) Field of Classification Search
USPC ........................................ 422/558; 73/864.41
See application file for complete search history.

(56) References Cited

U.S. PATENT DOCUMENTS

| 4,307,846 A * | 12/1981 | Spelsberg | B02C 19/0056 |
| | | | 241/246 |
| 5,224,658 A * | 7/1993 | Smith | G01N 1/286 |
| | | | 241/94 |
| 5,286,651 A * | 2/1994 | Smith | G01N 33/241 |
| | | | 850/16 |
| 5,829,696 A * | 11/1998 | DeStefano | B02C 19/08 |
| | | | 241/199.12 |
| 8,402,846 B2 * | 3/2013 | Mimori | B02C 19/08 |
| | | | 73/866 |
| 2017/0106366 A1 * | 4/2017 | Gross | B01L 3/5082 |
| 2019/0366327 A1 * | 12/2019 | Rettberg | G01N 33/1826 |

FOREIGN PATENT DOCUMENTS

DE 20201400232 U1 * 2/2014 ......... G01N 15/0266

OTHER PUBLICATIONS

Volatile Organic Chemical (VOC) Sampling Procedure, DOH Pub #331-220, by Washington State Department of Health, published before May 19, 2023.
Volatile Organic Compounds in Solids—PBM, Lab Manual Section, Lab Manual Section by British Columbia government, revision date: Mar. 15, 2016.

(Continued)

*Primary Examiner* — Daniel S Larkin
(74) *Attorney, Agent, or Firm* — Meagher Emanuel Laks Goldberg & Liao, LLP

(57) ABSTRACT

At least a method and an apparatus are provided for collecting, processing and/or measuring of volatile organic chemicals (VOCs) in a sample, particularly in a solid sample which needs to be crushed for the VOCs to be released. A solid sample is placed into a reusable vial made of e.g., a material having a crushing strength of at least 4000 pounds per square inch. The reusable vial is capped using an external capping unit. The sample can be crushed directly in same reusable vial with an external crushing pestle placed through the capping unit to release a volatile organic compound contained in the solid sample. The volatile organic compound contained in the solid sample can then be extracted from the same reusable vial for an analysis of the volatile organic compound.

20 Claims, 5 Drawing Sheets

(56) References Cited

OTHER PUBLICATIONS https://www.thermofisher.com/us/en/home/industrial/environmental/environmental-learning-center/contaminant-analysis-information/volatile-organic-compounds-analysis.html; Volatile Organic Compounds (VOC) Analysis website by ThermoFisher, published before May 19, 2023.
http://www.glassdynamicsllc.com/temperedglass.html, Tempered Glass—Safety Glass website by Glass Dynamics, LLC, published before May 19, 2023.
Brandon, J.R., Rock Mechanics Properties of Typical Foundation Rock Types—Summarizing Physical and Mechanical Tests of Rock Samples from Several Types of Foundation Sites, REC-ERC-74-10, Engineering and Research Center Bureau of Reclamation, Jul. 1974.
www.crdcreighton.com/wp-content/uploads/Rock-Classification.pdf, "Rock Classification" and "Concrete Classification" website by Drumcutters, published before May 19, 2023.
Matthew Kusinski, https://uwspace.uwaterloo.ca/bitstream/handle/10012/6535/Kusinski_Matthew.pdf, Application of Microwave-Assisted Technologies for the Analysis of Chlorinated Solvents in Rock Samples, 2012.
Carmen A. Lebron, et al., Contract Report CR-NAVFAC ESC-EV-1202, Dense Non Aqueous Phase Liquid (DNAPL) Removal from Fractured Rock Using Thermal Conductive Heating (TCH), Naval Facilities Engineering Command, Aug. 2012.
https://g360group.org/wp-content/uploads/2019/08/Core-DFN-Aug2019.pdf, COREdfn at Pace Analytic website, by Pace Analytical, Aug. 2019.
Beth L. Parker, et al. Discrete Fracture Network Approach for Studying Contamination in Fractured Rock, AQUA mundi (2012)—Am06052: 101-116, 2012.
Ronald A. Sloto, Hydrogeological Investigation at Site 5, Willow Grove Naval Air Station/Joint Reserve Base, Horsham Township, Montgomery County, Pennsylvania, Water-Resources Investigations Report 01-4263, 2002.
Adrian R. Lawrence et. al., A Method for Determining Volatile Organic Solvents in Chalk Pore Waters (Southern and Eastern England) and Its Relevance to the Evaluation of Groundwater Contamination, Journal of Contaminant Hydrology, 6 (1990) 377-386 377 Elsevier Science Publishers B.V., Amsterdam, 1990.
Specifications and Guidance for Contaminant-Free Sample Containers, United States Environmental Protection Agency Publication 9240.0-0SA, EPA540/R-93/051, PB93-9G3316, Dec. 1992.
Jonathan R. Kennel, Advances in Rock Core VOC Analyses for High Resolution Characterization of Chlorinated Solvent Contamination in a Dolostone Aquifer, A thesis presented to the University of Waterloo in fulfilment of the thesis requirement for the degree of Master of Science in Earth Sciences, 2008.
Part 1 (pdf pp. 1-200)—Jennifer Catherine Hurley, Rock Core Investigation of Dnapl Penetration and Persistence in Fractured Sandstone, A thesis presented to the University of Waterloo in fulfilment of the thesis requirement for the degree of Master of Science in Earth Sciences, 2003.
Part 2 (pdf pp. 201-401)—Jennifer Catherine Hurley, Rock Core Investigation of Dnapl Penetration and Persistence in Fractured Sandstone, A thesis presented to the University of Waterloo in fulfilment of the thesis requirement for the degree of Master of Science in Earth Sciences, 2003.
Part 1 (pdf pp. 1-70)—B335 Area RCRA Facility Investigation Work Plan—Former IBM East Fishkill Facility Hopewell Junction, New York, Prepared for IBM Corporation, File No. 2999.06, Sep. 2019.
Part 2 (pdf pp. 71-150)—B335 Area RCRA Facility Investigation Work Plan—Former IBM East Fishkill Facility Hopewell Junction, New York, Prepared for IBM Corporation, File No. 2999.06, Sep. 2019.
Part 3 (pdf pp. 151-240)—B335 Area RCRA Facility Investigation Work Plan—Former IBM East Fishkill Facility Hopewell Junction, New York, Prepared for IBM Corporation, File No. 2999.06, Sep. 2019.
Part 4 (pdf pp. 241-329)—B335 Area RCRA Facility Investigation Work Plan—Former IBM East Fishkill Facility Hopewell Junction, New York, Prepared for IBM Corporation, File No. 2999.06, Sep. 2019.
Richelle M. Allen-King et al., Final Report, A Field Method to Quantify Chlorinated Solvent Diffusion, Sorption, Abiotic and Biotic Degradation in Low Permeability Zones, SERDP Project, Jun. 2021.
Daniel J. Good et al., High-resolution delineation of chlorinated volatile organic compounds in a dipping, fractured mudstone: Depth- and strata-dependent spatial variability from rock-core sampling, Journal of Contaminant Hydrology vol. 171, Dec. 15, 2014, pp. 1-11.

* cited by examiner

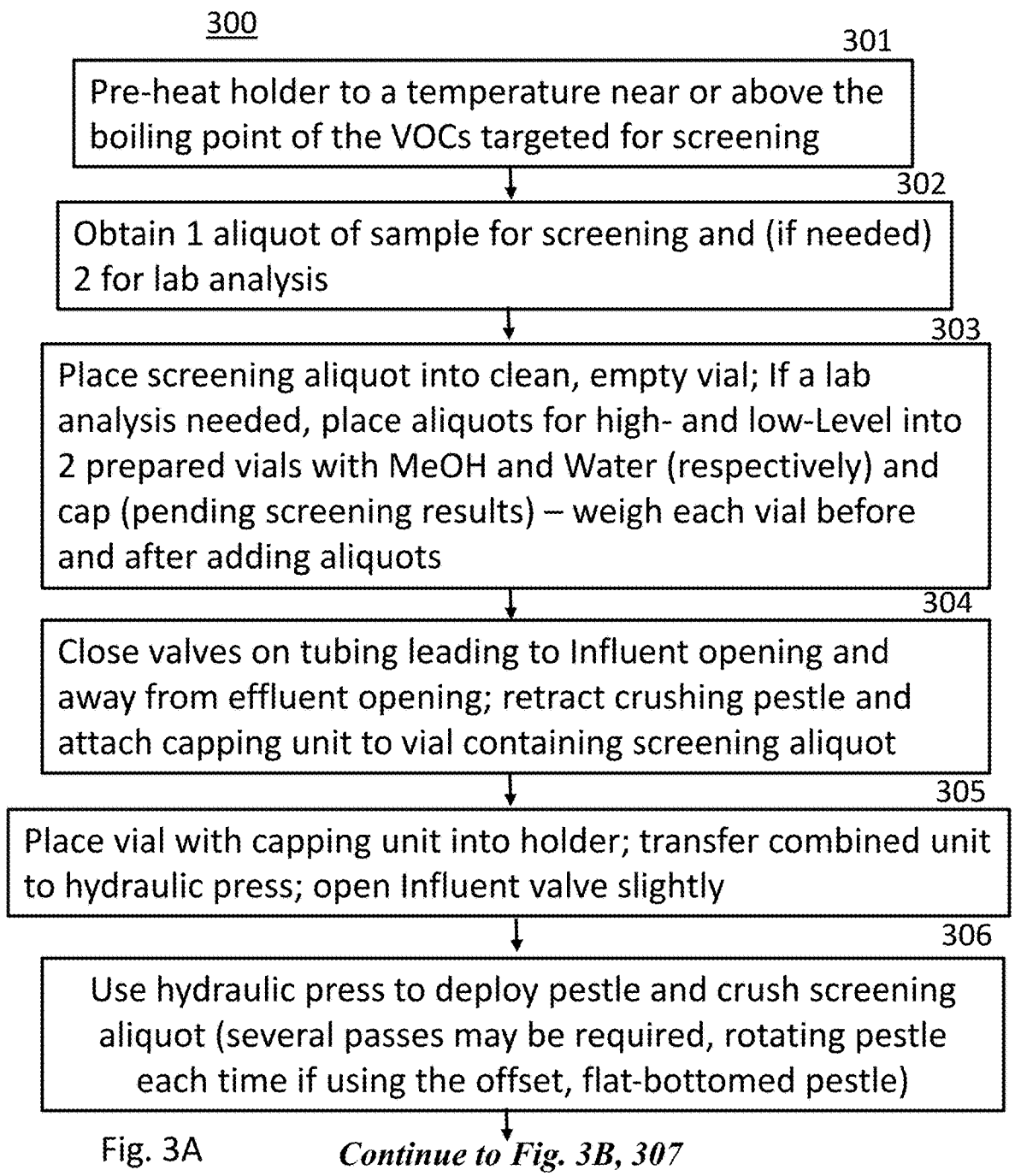
Fig. 3A   *Continue to Fig. 3B, 307*

300     *Continue from Fig. 3A, 306*

307 — Close influent valve; conduct heating of capped vial for pre-determined period of time (e.g., 10 minutes), consistent for all screenings

308 — Connect direct-reading organic vapor monitor (e.g., RAE Systems PPB-RAE) or vacuum container (e.g., Summa Canister, Tedlar bag in vacuum box) to effluent tubing downstream of valve with a valve Y fitting to temporarily draw ambient air only

309 — Open influent and effluent valves

310 — If direct-read screening, turn on organic vapor monitor and note initial and peak readings and those in a consistent time sequence/minimum duration (e.g., every 30 seconds for 5 minutes)

311 — If vacuum container screening, open vacuum container valve to draw air sample of sufficient volume for screening; close vacuum container valve and perform screening or laboratory analysis of the air sample

312 — Exemplary use of results of VOC screenings to inform selection of Low-Level or High-Level analytical methods for any corresponding lab analysis, and/or to provide a rapid, lower-cost proxy for Lab analysis, after correlation established

Fig. 3B

VOLATILE ORGANIC CHEMICAL IN SOLID SAMPLE COLLECTION, PROCESSING, AND MEASUREMENT APPARATUS AND METHOD

TECHNICAL FIELD

At least one of the present embodiments generally relates to an improved method or apparatus for collecting, processing and/or measuring of volatile organic chemicals (VOCs) in a sample, particularly in a solid sample which needs to be crushed for the VOCs to be released and analyzed.

BACKGROUND

VOCs are present in both synthetic and natural materials, so testing is done to ensure environmental and/or personal safety, as well as to verify that an environment or a product is in compliance with international VOC requirements. VOC is an acronym for Volatile Organic Compound. The term VOCs commonly refers to the list of compounds contained in EPA Method 8240 or the longer list of EPA Method 8260. Product manufacturers need to be aware of VOC requirements and make sure their products are compliant. Similarly, for example, testing is also done for soil or rocks from underground or a surrounding to ensure that, e.g., ground water or the surrounding is safe for humans.

EPA standard procedures exist for testing of both low-level VOCs (i.e., for concentrations in the range of 0.5 to 200 µg/kg, see EPA Method 5035—Closed-System Purge and Trap for Extraction of VOCs in Soil and Waste Samples), as well as high-level VOCs (i.e., for concentrations greater than 200 µg/kg, see EPA Method 5035—Sec. 2.2.2, $2^{nd}$ option). These procedures call for using a standard 40 ml glass VOA (volatile organic analysis) vial. VOA vials typically refer to typical, standard EPA approved 40 ml glass containers used for aqueous sampling of volatile compounds. Both procedures basically call for collecting and adding the samples in the field such as already unconsolidated solid matrix (e.g., usually soil or sediment, but not coherent solid formations or minerals) into the glass vial. The glass vial would typically already be pre-filled with some kind of preservative liquid (e.g., Sodium Bisulfate) or a purge and trap grade liquid (e.g., MeOH). Organic-free reagent water may also be added to the vials and the samples. In addition, a stir bar may be supplied with the vial which may be used to stir by hand the mixed sample with the added liquid(s). The vial is then capped and sealed typically with a threaded polypropylene cap, along with a TEFLON™ or PTFE-faced silicone septum insert, and transported to a laboratory for analysis.

Within a sample vial, the unoccupied area above a sample matrix is commonly referred to as the headspace. Using a static headspace, a sealed vial containing a collected sample may be heated to drive VOC compounds out of the sample matrix into an equilibrium with the gas phase. Once stabilized, the gas phase within the vial is then collected or transferred to an instrument for analysis. This technique is generally suited for compounds with relatively high Henry's law constants including fuel range organics and halogenated VOCs. However, this method may be unsuitable for MTBE or ethylene dibromide (EDB).

Another commonly used technique for VOC analysis is purge and trap concentration, also known as dynamic headspace sampling:

A sample is deposited into the sparging vessel where method analytes are purged from the water using a helium or other inert gas stream to sparge through the sample. As with static headspace, heat is sometimes applied to drive VOCs out of liquid phase and into the gas phase.

Once liberated from the sample, VOCs in the gas phase are transferred to an adsorbent trap where they will transiently bind. The trap may be dry purged for a short period to remove water.

The trap is then heated and back flushed with carrier gas to drive the analytes into a gas chromatographic analyzer for sampling and analysis.

In another technique, soil or crushed rock extracts undergo supplemental, microwave assisted extraction (MAE). In one application of this method, the MAE takes place using the 40 ml glass VOA vial in which the sample is collected in the field as the extraction vessel. This avoids the need for a transfer into a separate vessel (with inherent loss of VOCs) and is made possible by the microwave-transparency of the glass container material.

Current EPA approved 40 ml VOA glass vials are typically made out of borosilicate glass. The crushing strength ratings of borosilicate glass typically range from 90 PSI (pounds per square inch) to 600 PSI depending on end finish, diameter, and length required. Borosilicate glass is used to manufacture these glass vials because it has good chemical and thermal resistance. However, these glass vials need to be handled with great care since they may be prone to crack or break under pressure or stress. Also, these glass vials are usually disposable, just for one time use.

SUMMARY

The drawbacks and disadvantages of the prior art are solved and addressed by one or more aspects described herein.

Therefore, according to an embodiment, a method is presented. The method comprises placing a solid sample into a vial wherein the vial is made of a material having a crushing strength of at least 4,000 pounds per square inch; capping the vial using a capping unit; and crushing the sample directly in same vial with an external crushing pestle placed through the capping unit to release a volatile organic compound contained in the solid sample.

According to another embodiment, a system is presented. The system comprises a vial made of a material having a crushing strength of at least 4,000 pounds per square inch for collecting a solid sample, wherein the vial comprising threads at a top portion of the vial; a capping unit configured to thread onto the threads of the vial for providing a connection with the vial; and an external crushing pestle placed through a circular center of the capping unit, wherein the external crushing pestle is configured to crush the sample directly in same vial to release a volatile organic compound contained in the solid sample into an extraction solvent contained within the vial.

BRIEF DESCRIPTION OF THE DRAWINGS

FIGS. 3A and 3B illustrate another exemplary process according to aspects of present embodiments.

DETAILED DESCRIPTION

Figure 1A:
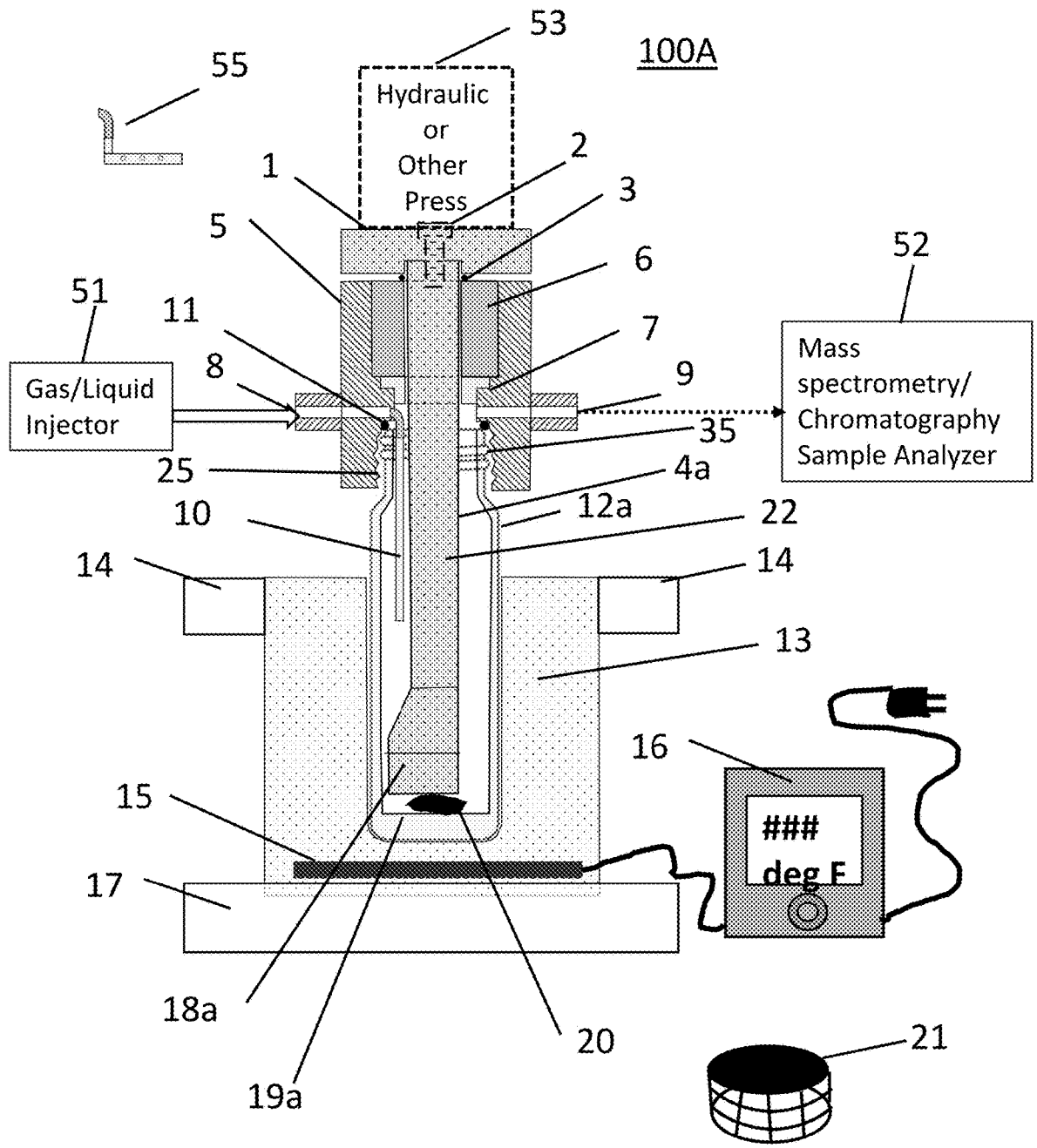
FIG. 1A illustrates an exemplary system according to aspects of present embodiments.

Present inventor recognizes that the existing VOC collection glass vial and its associated collection methods and systems have many disadvantages which can be improved upon by the present improved embodiments. For example, if a solid sample (e.g., a hardened mineral formation, rock or concrete, not just unconsolidated soil) is crushed in a space with exposure to air or without prior immersion in an extraction solvent, significant VOC losses will occur both upon crushing and during transfer to the sample vial after crushing. Additionally, if other solvents or liquids have to be added to the sample, the cap of the original collection glass vial will need to be opened for an extended period of time which will risk even more escaping of the VOCs in the original collection vial, and therefore previous and existing systems and methods will not provide an accurate measurement of the VOC contents of the collected solid sample.

In contrast, present embodiments allow a user to more efficiently collect and accurately measure the VOC contents of a collected sample, especially a solid sample, in a seamlessly way, using an improved collection system and method. In particular, the improved collection system and method comprises an improved hardened collection vial, along with an external capping unit for an easy assertion of an external crusher through the external capping unit for crushing the sample directly in the same collection vial.

The improved collection vial is not made out of breakable glass, but with a hardened, non-porous material, such as, e.g., metal, advanced ceramic or other hardened thermal and chemical resistant material which can withstand a crushing force of the external crusher. In one embodiment, the improved collection vial can withstand at least 700 PSI of force which is much higher than a typical present EPA 40 ml glass vial made out of borosilicate glass which can only withstand up to about 600 PSI of force, as described previously.

In another embodiment, the improved collection vial can withstand at least 1000 PSI or even 2000 PSI of force or higher for hard rock. In one embodiment, the material to be used to make these improved vials may comprise, e.g., non-porous, non-magnetic stainless steels, titanium, or advanced ceramics (e.g., alumina and zirconia), or advanced composites (e.g., ceramic glass). These classes of materials have compressive and tensile yield strengths of at least 15,000 PSI or greater. Accordingly, in one embodiment, improved vials are made of a material having a strength of at least 15,000 pounds per square inch, so that the collected material may be collected and crushed directly in the same vial.

In yet another embodiment, the improved collection vial can be made of a material that exhibits the strength and chemical properties noted above, but which is also microwave-transparent (e.g., certain advanced ceramics (e.g., alumina) and certain advanced composites (e.g., ceramic glass). In addition, some microwave-transparent materials which may exhibit slightly lesser strengths, such as modified fluoropolymer (e.g., TFM—TEFLON™ modified polytetrafluoroethene) may also be used in this embodiment. Accordingly, owing to the microwave-transparency of the materials in this embodiment, the rock samples could be crushed without VOC loss (as in the prior embodiments) and later subjected to MAE, using the same vial as the MAE extraction vessel, obviating need for transfer of sample to a separate MAE extraction vessel, and thereby avoiding related VOC losses. Accordingly, an embodiment is disclosed that uses the modified fluoropolymer (e.g., TFM—TEFLON™ modified polytetrafluoroethene) material which has a material strength of at least 4000 PSI for making an EPA 40 ml compatible vial.

Furthermore, the present inventor recognizes that rocks exhibit uniaxial compressive strengths ranging from approximately 1,500 to 6,000 PSI for soft sedimentary rock, such as siltstone and shale, soft limestones and dolomites; up to about 15,000 PSI for harder, mostly crystalline rocks, such as sandstone, conglomerate, dense limestones and dolomites, argillite, vesicular basalt and weathered granites; and up to 25,000 PSI for dense, hard crystalline rocks, such as quartzite, granite, granodiorite, basalt, gabbro and dense gneisses (see, e.g., Brandon, J. R., 1974. Rock mechanics properties of typical foundation rock types (No. REC-ERC-74-10); and Drumcutters Website, accessed May 2023, "Rock Classification" and "Concrete Classification" www.crdcreighton.com/wp-content/uploads/Rock-Classification.pdf). Concrete has uniaxial compressive strengths typically in the range 2,000 up to 10,000 PSI (see Drumcutters, 2023). These values reflect measurements made during testing of trimmed, cylindrical samples in a geotechnical testing laboratory as disclosed in published literatures.

In a hydraulically driven rock crusher with a pestle (as in the current disclosed embodiments), a pressure is applied not to idealized test cylinders of rock or concrete, but instead to irregularly shaped chip samples. Pressures that must be applied to crush the chip samples can be significantly lower than the stated compressive strengths. For example, Hurley (Hurley, J. C. 2003, Rock core investigation of DNAPL penetration and persistence in fractured sandstone, Master's thesis, Earth Sciences Department, University of Waterloo) found that " . . . an applied pressure of 3000 to 4000 PSI . . . was enough to reduce sandstone samples to sand-sized particles and siltstone and shale samples to wet mud." Work by Kennel (Kennel, J. R., 2008, Advances in Rock Core VOC Analyses for High Resolution Characterization of Chlorinated Solvent Contamination in a dolostone Aquifer, MSc thesis, Earth Sciences Department, University of Waterloo, Waterloo, ON.) entailed study of dolostones and dense, cherty dolostones wherein crushing was achieved by applying 4000-7000 PSI to each rock sample. This likely reflects the fact that some of the crushing takes place by tensile failure (tensile strengths of rocks and concrete are typically two to ten (or more) times lower than respective compressive strengths). Accordingly, these studies also support that 4000 PSI is a good selection for a minimum material strength to make a EPA compatible vial according to the present embodiments. In other embodiments, the material strength may have a minimum crushing strength of 1) 1500 PSI 2) 6000 PSI, 3) 10000 PSI, 4) 15000 PSI and 5) 25000 PSI to be able to handle the crushing pressure required to crush the different types of materials.

The external capping unit of the present embodiments may also comprise respective influent and effluent openings for, e.g., injection of external fluids or gases into the improved hardened collection vial, and for extraction of gases or fluids from the improved hardened collection vial for, e.g., headspace evacuation, sample screening, processing, and etc. Therefore, the improved collection system and method, by including an improved hardened collection vial and its associated improved external processing elements, together provide (among other advantages): 1) collection of the solid sample, 2) crushing of the solid matrix sample, 3) adding of VOC solvents or gases, 4) heating of the sample, and 5) extraction of the sample for analysis and/or sampling, all in the same self-contained collection vial.

Present improved embodiments therefore eliminate a step with air-exposed crushing and subsequent transfer from a crusher cup to a sample vial, with the associated sample losses and inaccuracies. In contrast, in the present embodiments, the collection vial, the crusher cup and sample vessel become all the same unit. Present improved embodiments also enable maintenance of a headspace condition that precludes ignition of MeOH or other flammable extraction solvent. Furthermore, present embodiments enable pre-screening of VOCs liberated upon dry-crushing of a split (or separate fraction) of sample, to correlate with extract analyses and enable high-frequency use as a field screening method. Present embodiments also enable pre-screening of VOCs liberated upon dry-crushing of a split sample, to guide the selection of an appropriate high level or low level VOCs analytical method.

Accordingly, FIG. 1A presents an example of an improved system 100A. In system 100A, an improved vial 12a may be made of, e.g., non-magnetic metal, advanced ceramic or other materials, instead of glass, to still enable use of a magnetic stirring bar as needed, as envisioned in EPA method 5035. Materials for the improved vial 12a may be, for example, a hardened and corrosion resistant non-magnetic alloy of stainless steel; titanium alloy; advanced ceramic, advanced composite, modified fluoropolymer or other chemically resistant material. In an embodiment shown in FIG. 1A, vial 12a has a flat inner base surface 19a. In an embodiment, a crushing pestle 4a and a vial 12a may be manufactured using materials that can withstand contact with a sample, water, MeOH, sodium bisulfate water preservatives without reacting with those elements in such a way as to interfere with or otherwise cause non-representative results from the analysis, or wearing out and becoming unusable prematurely.

In any case, exemplary material for the vial 12a is strong enough to allow an external pestle 4a to be used to crush and/or grind a collected solid sample 20 placed on the bottom of the vial 12a, without deforming the vial 12a. In addition, the external shape and size (including the size of the treads 35) of the vial 12a would essentially be the same as a standard EPA approved 40 ml VOA glass vial, so that other existing accessories and analysis instruments may still be used with the present embodiments, without major modifications.

As shown in FIG. 1A, a field collection cap 21 may also be provided with the improved vial 12a for use in the field to cap the improved vial 12a after the sample has been collected and placed into the vial 12a. The field collection cap 21 has corresponding threads that will fit tightly to the threads 35 on the top portion of the improved vial 12a. Furthermore, since the improved vial is in the same size and shape (including the treads) as the existing EPA approved VOA glass vial, the field collection cap 21 may also be, e.g., the same as a cap commonly used for an EPA approved VOA glass vial, which is typically a threaded polypropylene cap with a TEFLON™ Teflon or PTFE-faced silicone septum insert as previously described.

Additionally, since the improved vial 12a has the same outer shape and size as the existing EPA approved VOA glass vial, the improved vial 12a would fit into the same collection tray or analysis tray used to sort and analyse the content of the vial by existing VOC sorting and/or analysis systems, without major modification. One example of such a VOC automated analysis system with multiple trays to sample multiple EPA VOA standard vials is the 4100 Water and Soil Sample Processor, made by OI Analytical located at College Station, Texas.

As shown in FIG. 1A, system 100A has the external crushing pestle 4a which is placed through a circular center opening of a capping unit 5. The external crushing pestle 4a has an offset, flat base 18a for crushing a solid material 20 inside the improved vial 12a. The offset base 18a is offset to one side from the center of capping unit 5. In one embodiment, the pestle 4a may be used to crush the solid material 20 in several passes, either by rotating the pestle 4a or the vial 12a by, e.g., 120 degrees between each pass. In one embodiment, such a rotational movement may be done by using a respective motor connected therewith (not shown) as is well known in the art.

In an embodiment, the crushing pestle 4a and the a-vial 12a are both manufactured using materials that can withstand contact with a sample, water, MeOH, sodium bisulfate or other corrosive, chemically active water preservatives without reacting with those elements in such a way as not to interfere with or otherwise cause non-representative results from the analysis, or wearing out and becoming unusable prematurely. Again, the materials may be, e.g., a metal, such as stainless steel or titanium alloy or advanced ceramic or advanced composite which can withstand a crushing force of at least 15,000 PSI and provide good thermal and chemical resistance.

Also as illustrated in FIG. 1A, the top portion of the external crushing pestle 4a is connected to a load bearing plate 1 via a connecting member such as, e.g., a screw 2. The load bearing plate 1 may be made of, e.g., hard, corrosion resistant material, such as, e.g., stainless steel, titanium alloy, and etc. The load bearing plate 1 is used to transfer a pressing force from a pressure applying implement 53, such as a hydraulic press, piston, or other type of pressure applying machines to press down on the load bearing plate 1 (and therefore the pestle 4a), for crushing a solid material 20. In an embodiment, the pressure applying implement 53 is an automated machine. In an embodiment, the pressure applied to the load bearing plate 1 by the pressure applying implement 53 may be at least 15,000 PSI, to ensure that the sample 20 can be crushed sufficiently by the pestle 4a to release the VOCs.

In addition, a pestle O-ring 3 is situated below the load bearing plate 1 and surrounds the top portion of the pestle 4a. The O-ring 3 may be made out of, e.g., rubber, plastic or polyurethane. Accordingly, pestle O-ring 3 provides a vertical limit and/or damping effect on the downward movement of the pestle 4a.

System 100A in FIG. 1A also comprises the external capping unit 5 which has threads 25. Threads 25 fit securely onto threads 35 of vial 12a, and along with an external capping unit O-ring 11, provide an air tight seal of vial 12a when they are threaded and connected together. The external capping unit 5 may be made of materials such as, e.g., a metal, such as stainless steel or titanium or advanced ceramic, as described previously. The top portion of the external capping unit 5 also comprises a slide bushing 6 along the top inner wall of the external capping unit 5. The slide bushing 6 is a sleeve bearing which may be made of materials, such as, e.g., ultra-high molecular weight (UHMW) polyethylene, TEFLON™ or other hard, slippery material that is chemically resistant. The slide bushing 6 helps to align the pestle 4a and guides it vertically during a crushing operation of the sample 20. Furthermore, external capping unit 5 comprises an influent opening 8 and an effluent opening 9 respectively for, e.g., injection of external additives such as fluids or gases into the improved hardened collection vial 12a, and for extraction of gases or fluids from the improved hardened collection vial 12a for, e.g., headspace evacuation, sample screening, processing and/or analysis, etc.

In addition, various injection and evacuation tubes and valves (not shown) may be connected to the influent opening 8 and the effluent opening 9 respectively, for the injection and evacuation processes. In one exemplary embodiment as shown in FIG. 1A, a drop tube 10 may be additionally connected to the influent opening 8 to facilitate the injections of liquids or gases, such as, e.g., nitrogen, ambient or filtered air, or other fluids, toward the base of the interior of the vial 12a. A drop tube 10 would also promote a circulation of gases upward from the base 19a of the interior of the vial 12a, toward the effluent opening 9. In another embodiment, an extraction tube (not shown) may be similarly and respectively connected (i.e., similar to drop tube 10) to the effluent opening 9 to facilitate the extraction processes. As shown in FIG. 1A, the injection of the external fluids or gases may be performed by a gas/liquid injector 51 connected via a tubing and valves to the influent opening 8. The effluent opening 9 may be similarly connected by a tubing and valve assembly to a mass spectrometry analyzer, a chromatography sample analyzer, or other type of gas/liquid analyzer 52, as shown in system 100A of FIG. 1A.

In addition, system 100A in FIG. 1A comprises a pestle rod wiper seal 7. Wiper seals (also known as scraper seals) are axial seals that form a tight fit but still allow a reciprocating ram rod, such as pestle 4a, to pass through the seal's inner bore. Pestle rod wiper seal 7 may be made of a combined metal material, such as, e.g., corrosion resistant carbon steel or stainless steel combined and bonded with flexible non-metal material such as, e.g., chemical resistant nitrile, polyurethane, rubber, plastic, etc. The pestle rod wiper seal 7 also provides an air-tight seal around cylindrical shaft 22 of pestle 4a and prevents any liquid and/or solid seeping from vial 12a from contacting and fouling the slide bushing 6.

In an embodiment, system 100A may comprise a heatable vial holder 13 which holds the vial 12a in a vertical and stable position, even during the crushing/grinding of the sample 20 by pestle 4a. The heatable vial holder 13 may be made of, e.g., corrosion resistant stainless steel. The heatable vial holder 13 may further comprise on its top portion, insulating vessel holder handles 14 which would allow handling and movement of heatable vial holder 13. The insulating vessel holder handles 14 may be made of a heat resistant plastic, such as e.g., phenolic resin or other insulating materials.

The heatable vial holder 13 is heatable by, e.g., a heating element 15 which is controlled by a heating element/heater controller 16. Heating element/heater controller 16 is able to control and read out the heating temperature provided to heat vial 12a, through the heating element 15. The heating temperature provided to heat the vial 12a may be targeted, e.g., to a known boiling point or ranges of boiling points of VOCs anticipated to be present in the sample being screened.

In an embodiment, system 100A may further comprise an insulating base 17 which provides additional support and insulation to the base of the heatable vial holder 13. The insulating base 17 provides a solid, thermally insulated base for use during screening, and to limit a transfer of heat from the heatable vial holder 13 to/from other implements of system 100A.

In an embodiment, the external crushing pestle 4a may be deployed in a gradual, non-percussive manner to limit splashing and potential sample losses and inaccuracy. In an embodiment, the external crushing pestle 4a and the volume of the vial 12a may accommodate EPA Method 8260 sample and solvent quantities without overflow, while keeping a solid material, such as a rock or other minerals submerged at all times. In an embodiment, the improved vial 12a may be sufficiently light, together with sample and extract to be weighable to within 0.01 gram of accuracy using a portable field balance.

In an embodiment, the proposed shapes of the external crushing pestle (4a in FIG. 1A or 4b in FIG. 1B) are aimed to crush a solid sample to a consistency of coarse sand and smaller particles, with as few passes pressed into the sample as possible, without compacting it back into a solid mass. In addition, the external crushing pestle would not jam during the crushing process and may be largely self-cleaning on retraction from solvent/rock mix, without retaining sample residue. In this regard, the present inventor recognizes that prior crushers with a waffle like pressing surface tend to retain more sample residues and are not as desirable as a pestle with a smooth pressing surface.

In an embodiment, instead of just using a single system 100A as shown in FIG. 1A (or system 100B to be shown in FIG. 1B and described later) to analyze a single vial 12a, multiple systems 100 As may be deployed side by side, using, e.g., a multi-sample crushing and/or sampling rack. The multi-sample crushing and/or sampling rack may hold steadily a number of individual combinations made of a respective crushing pestle 4a and a respectively vial 12a. The multiple crushing pestles may then be driven and pressed by, e.g., multiple machine presses or just one single machine press.

In an embodiment, system 100A may additionally include a dosing syringe (not shown) for adding an initially reserved portion of the MeOH or water called for in EPA Method 8260, to rinse sample post-crush residue from pestle into vial, with the MeOH or water discharged around the circumference of the pestle rod by way of a specially-designed modified drop tube 55, which may be fitted to influent opening 8 (or another duplicate influent opening—not shown).

Figure 1B:
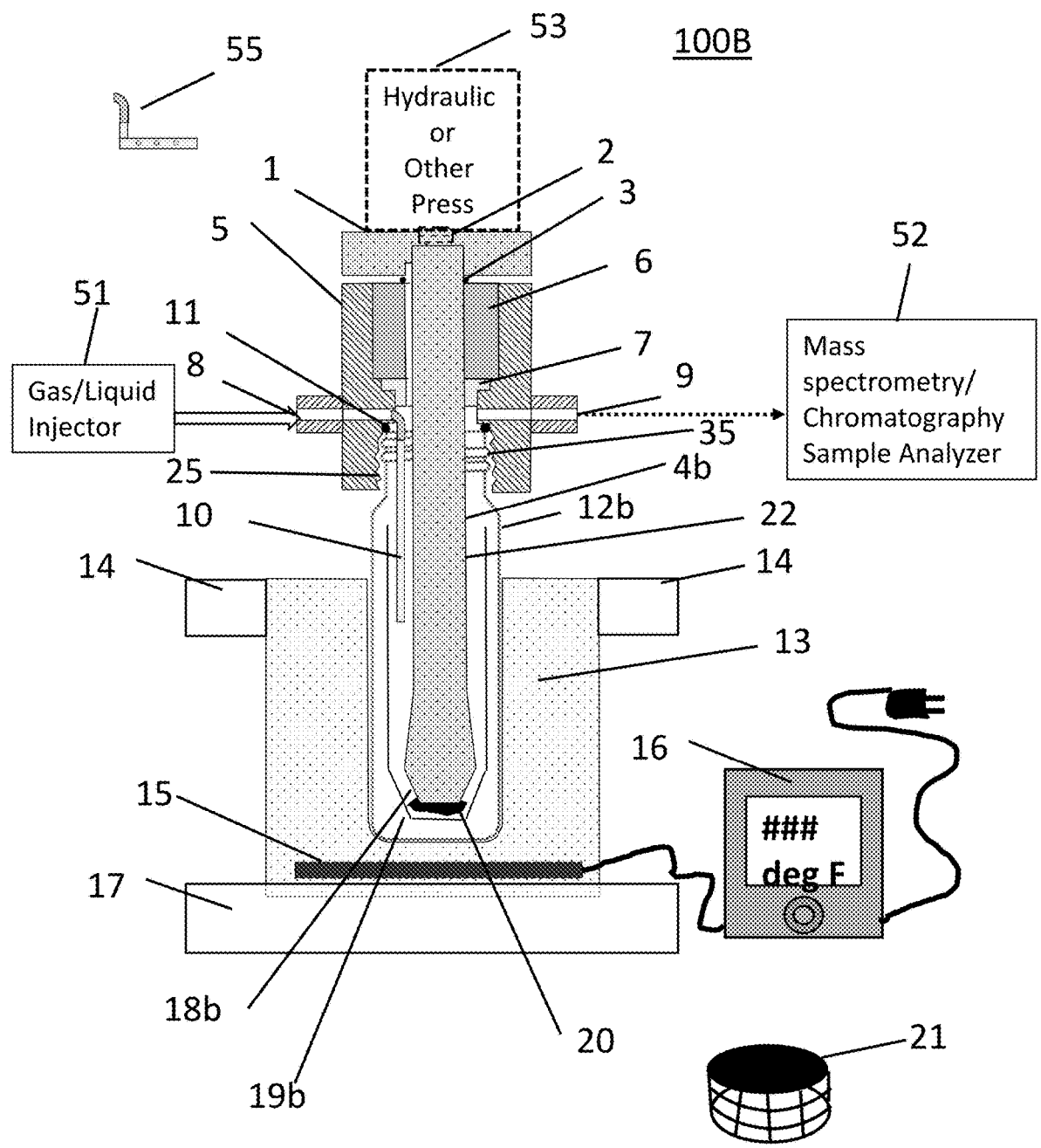
FIG. 1B illustrates another exemplary system according to aspects of present embodiments.

FIG. 1B shows another exemplary system 100B according to aspects of the present embodiments. System 100B in FIG. 1B is similar to system 100A in FIG. 1A, except:
  1) The shape of the base 19a of vial 12a of system 100A in FIG. 1A, compared with the shape of the base 19b of vial 12b of system 100B in FIG. 1B. The base 19a of the vial 12a in system 100A is flat and is essentially perpendicular to the side walls of vial 12a. In contrast, the base 19b of the vial 12b in system 100B is in a tapered shape.
  2) The shape of the external crushing pestle 4a of system 100A in FIG. 1A, compared with the shape of the external crushing pestle 4b of system 100B in FIG. 1B. In system 100A, the base 18a of pestle 4a is offset to one side of the center of the capping unit 5 and the base 18a has a flat surface. In contrast, the base 18b of pestle 4b in system 100B is in a bevel shape to exert shearing on sample material when pressed into the differently tapered shape of the base 19b of vial 12b.

In an embodiment, the improved vial (12a of FIG. 1A or 12b of FIG. 1B) is reusable after appropriate cleaning. This is different than and has a clear advantage over the existing glass vial which is usually discarded after use.

Figure 2:
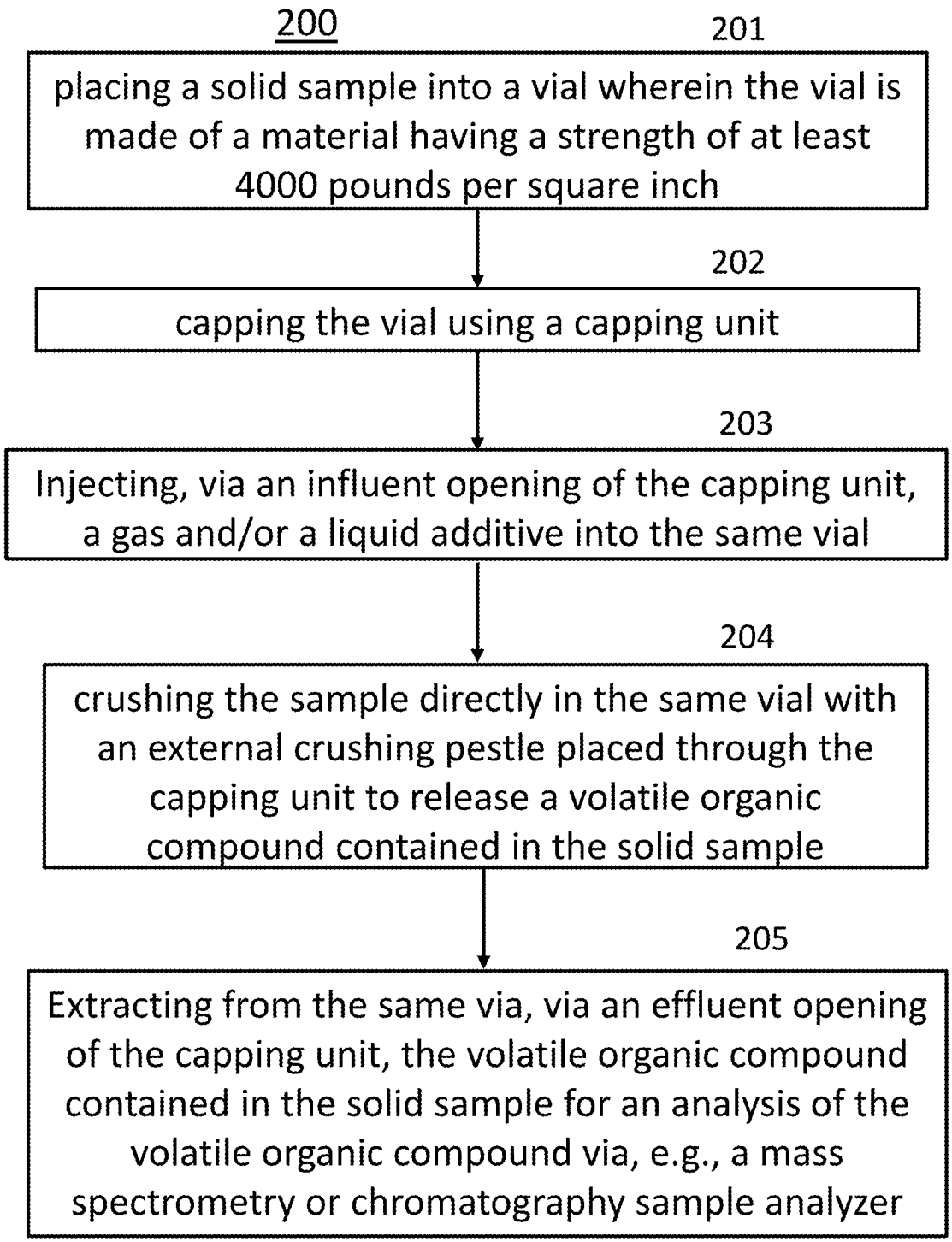
FIG. 2 illustrates an exemplary process according to aspects of present embodiments.

FIG. 2 illustrates an exemplary process 200 in which various aspects and embodiments are implemented, using system 100A or 100B as described previously. At step 201 of FIG. 2, a solid sample is placed into the improved collection vial (12a of FIG. 1A or 12b of FIG. 1B) wherein the vial is made of a material having a crushing strength of at least 4,000 pounds per square inch. At step 202 of FIG. 2, the same vial is capped using a capping unit (5 of FIG. 1A or FIG. 1B). At step 203 of FIG. 2, a gas (e.g., an inert gas, such as a nitrogen, or a liquid additive is injected, via an influent opening (8 of FIG. 1A or FIG. 1B) of the capping unit to the same vial. At step 204 of FIG. 2, the sample is crushed directly in the same vial with an external crushing pestle (4*a* of FIG. 1A or 4*b* of FIG. 1B) placed through the capping unit to release a volatile organic compound contained in the solid sample. At step 205 of FIG. 2, the volatile organic compound contained in the solid sample is thereafter extracted, via an effluent opening of the capping unit (9 of FIG. 1A or FIG. 1B), from the same vial for an analysis of the volatile organic compound. The analysis of the extracted volatile organic compound is typically done via a sample analyzer, such as e.g., a mass spectrometry or chromatography sample analyzer (52 of FIG. 1A or FIG. 1B).

In an embodiment, as mentioned before, the improved collection vial (12*a* of FIG. 1A or 12*b* of FIG. 1B) may be used as a collection vial or a pre-screening vial before the final sample is to be sent to a lab for additional or more detailed analysis. In those instances, extraction solvents (e.g., MeOH, distilled water) as specified and in volumes noted in the intended preparation and analytical methods (e.g., EPA Methods 5035 and 8260) may be added to the vial in the field, when the sample is placed into the vial. Additionally, an inert gas (e.g., nitrogen) may also be introduced to flush oxygen from the headspace and thereby diminish the probability of ignition of headspace vapors. Additionally, a magnetic stirrer bar may be supplied with the vial to a field or lab personnel. Thereafter, the vial is capped and the vial may be transmitted to the laboratory under an appropriate chain-of-custody for analysis according to the selected analytical method.

FIGS. 3A and 3B illustrate another exemplary process 300 according to aspects of the present embodiments. FIG. 3A illustrates steps 301 to 306 of the exemplary process 300 and FIG. 3B illustrates the continuation of the exemplary process 300 with steps 307 to 312 of the process 300. These steps 301 to 312 of the process 300 provide detailed descriptions of how an aliquot of sample may be prepared for screening and/or analysis according to the present embodiments.

Accordingly, the present embodiments provide an improved, efficient and controlled environment allowing flushing of interior headspace with inert gas (e.g., nitrogen), enabling safe crushing of the sample directly into an extraction solvent (e.g., methanol)—necessary to diminish or entirely prevent crushing-related loss of targeted volatile organic compounds from the sample—with limited risk of ignition, and potentially in conjunction with MAE supplemental extraction, all using the same collection vial. The present embodiments also eliminate physical loss of sample as crusher cup residue, unlike previous systems and methods.

Present embodiments reduce or even eliminate potential sources of VOC loss associated with existing methods; and offer more efficient, cost-effective applications, as well as unique field-screening capabilities. With present embodiments, sample crushing takes place directly into extraction solvent within a specially designed combination crusher vessel/sample container, eliminating both air contact and sample transfer related VOC losses. Furthermore, present embodiments may incorporate influent and effluent fittings and a controlled heatable base that enable specialized sample headspace screening. Present embodiments may also be subject to microwave assisted extraction.

Sample processing for lab analysis according to the present embodiments may be done either directly in the field or, in an application, in the laboratory itself. In the latter case, field crews are responsible only for placing weighed samples of the consolidated, solid-matrix material into a novel combined crusher vessel/sample container, which has extraction solvent(s) previously added during preparation by the laboratory. Samples are kept upright after collection, to ensure continuous immersion in the extraction solvent(s) until processing is performed at the laboratory using the crusher elements of the present embodiments.

Therefore, consequential improvements provided by the present embodiments are numerous and may include, but are not limited to, e.g., groundwater rock matrix diffusion studies. As one additional example, present embodiments may be used to achieve more accurate detection of in-place VOC concentrations for subsurface vapor intrusion source identification, especially in the context of contaminated land and site redevelopment. In such instances, use of the present embodiments may support improved detection of VOC concentrations in concrete or other solid-matrix building materials; or in near-surface bedrock at former locations of buildings where VOCs were utilized or discharged during prior operations.

The present embodiments may also be used, for example, in oil or gas explorations to sample contents of extracted rocks or minerals.

In the present patent specification, when a figure is presented as a flow diagram, it should be understood that it also provides a block diagram of a corresponding apparatus. Similarly, when a figure is presented as a block diagram, it should be understood that it also provides a flow diagram of a corresponding method/process.

Reference to "one embodiment" or "an embodiment" or "an embodiment" or "one implementation" or "an implementation", as well as other variations thereof, means that a particular feature, structure, characteristic, and so forth described in connection with the embodiment is included in at least one embodiment. Thus, the appearances of the phrase "in one embodiment" or "in an embodiment" or "in one implementation" or "in an implementation", as well any other variations, appearing in various places throughout this application are not necessarily all referring to the same embodiment.

Additionally, this application may refer to "determining" various pieces of information. Determining the information can include one or more of, for example, estimating the information, calculating the information, predicting the information, or retrieving the information from memory.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as is clear to one of ordinary skill in this and related arts, for as many items as are listed.

We describe a number of embodiments. Features of these embodiments can be provided alone or in any combination.

The invention claimed is:

1. A system comprising:
   a vial made of a material having a crushing strength of at least 4000 pounds per square inch configured for collecting a solid sample, wherein the vial comprising threads at a top portion of the vial;
   a capping unit configured to thread onto the threads of the vial for providing a connection with the vial; and
   an external crushing pestle placed through a circular center of the capping unit, wherein the external crushing pestle is configured to crush the sample directly in same vial to release a volatile organic compound contained in the solid sample.

2. The system of claim 1 wherein the capping unit further comprising an influent opening configured to inject an additive into the same vial and an effluent opening configured to extract the volatile organic compound contained in the solid sample from the same vial for an analysis.

3. The system of claim 2 wherein the additive is a gas.

4. The system of claim 2 wherein the additive is a liquid.

5. The system of claim 2 further comprising a mass spectrometry analyzer or a chromatography sample analyzer for the analysis.

6. The system of claim 1 further comprising a hydraulic press configured to apply a pressing force to the external crushing pestle.

7. The system of claim 1 wherein the vial has an outer shape and size of an EPA approved 40 ml glass VOA (volatile organic analysis) vial.

8. The system of claim 1 wherein a base of the external crushing pestle is offset to one side of a center of the capping unit.

9. The system of claim 1 wherein a base of the external crushing pestle is in a bevel shape.

10. The system of claim 1, further comprising a heating element configured to heat the vial.

11. A method, comprising:
    placing a solid sample into a vial wherein the vial is made of a material having a crushing strength of at least 4000 pounds per square inch;
    capping the vial using a capping unit; and
    crushing the sample directly in the same vial with an external crushing pestle placed through the capping unit to release a volatile organic compound contained in the solid sample.

12. The method of claim 11 further comprising:
    injecting an additive into the same vial.

13. The method of claim 12 wherein the injecting is done via an influent opening of the capping unit.

14. The method of claim 13 further comprising extracting from the same vial the volatile organic compound contained in the solid sample for an analysis of the volatile organic compound wherein the extracting is done via an effluent opening of the capping unit.

15. The method of claim 14 wherein the analysis is performed via a mass spectrometry analyzer or chromatography sample analyzer.

16. The method of claim 11 wherein the crushing further comprising applying pressure to the external crushing pestle via a hydraulic press.

17. The method of claim 11 wherein the vial has an outer shape and size of an EPA approved 40 ml glass VOA (volatile organic analysis) vial.

18. The method of claim 11 wherein a base of the external crushing pestle is offset to one side of a center of the capping unit.

19. The method of claim 11 wherein the vial is reusable after cleaning.

20. The method of claim 12, further comprising heating the vial via a heating element.

* * * * *